US012751692B2

(12) United States Patent
Beqiri et al.

(10) Patent No.: US 12,751,692 B2
(45) **Date of Patent: *Oct. 6, 2026**

(54) ASSESSING HEART PARAMETERS USING NEURAL NETWORKS

(71) Applicant: ULTROMICS LIMITED, Oxfordshire (GB)

(72) Inventors: Arian Beqiri, Oxfordshire (GB); Andrew Parker, Oxfordshire (GB); Jurriath Azmathi Mumith, Oxfordshire (GB); Gary Woodward, Oxfordshire (GB); Deborah Markham, Oxfordshire (GB); Ross Upton, Oxfordshire (GB)

(73) Assignee: ULTROMICS LIMITED, Oxfordshire (GB)

(*) Notice: Subject to any disclaimer, the term of this patent is extended or adjusted under 35 U.S.C. 154(b) by 0 days.

This patent is subject to a terminal disclaimer.

(21) Appl. No.: 19/026,869

(22) Filed: Jan. 17, 2025

(65) Prior Publication Data

US 2025/0152131 A1 May 15, 2025

Related U.S. Application Data

(63) Continuation of application No. 17/905,688, filed as application No. PCT/GB2021/050563 on Mar. 5, 2021, now Pat. No. 12,207,968.

(30) Foreign Application Priority Data

Mar. 6, 2020 (GB) ..................................... 2003346
Mar. 6, 2020 (GB) ..................................... 2003347

(51) Int. Cl.
*A61B 8/08* (2006.01)
*A61B 8/00* (2006.01)
(Continued)

(52) U.S. Cl.
CPC ............ *A61B 8/0883* (2013.01); *A61B 8/481* (2013.01); *A61B 8/485* (2013.01); *G06N 3/045* (2023.01); *G06N 3/08* (2013.01)

(58) Field of Classification Search
CPC ....... A61B 8/065; A61B 8/0883; A61B 8/463; A61B 8/466; A61B 8/481; A61B 8/483;
(Continued)

(56) References Cited

U.S. PATENT DOCUMENTS 6,106,466 A 8/2000 Sheehan
10,631,828 B1 * 4/2020 Hare, II ................ G16H 30/20
(Continued)

FOREIGN PATENT DOCUMENTS

JP 2017164076 A 9/2017
JP 2018535781 A 12/2018
(Continued)

OTHER PUBLICATIONS

Decision to Grant a Patent dated Jul. 11, 2025 in Japanese Patent Application No. 2022-553614.

*Primary Examiner* — Mark D Remaly
(74) *Attorney, Agent, or Firm* — Meunier Carlin & Curfman LLC

(57) ABSTRACT

An embodiment of the invention provides a system for automatically deriving a parameter of a human heart from ultrasound results. A first neural network is arranged to receive a plurality of echocardiographic images and to classify the images into one of at least a two-chamber view and a four-chamber view. A second neural network is arranged to receive echocardiographic images comprising a two- or four-chamber view and to identify the endocardial border of the left ventricle (LV) for each view. End-systole and end-diastole images are then identified and a parameter
(Continued)

| Model | Dice Coefficient(%) |
|---|---|
| Non-contrast A2C/A4C views | 92.47 |

such as LV volume, ejection fraction, global longitudinal strain and regional longitudinal strain is calculated.

11 Claims, 5 Drawing Sheets

(51) Int. Cl.

| | |
|---|---|
| ***G06N 3/045*** | (2023.01) |
| ***G06N 3/08*** | (2023.01) |

(58) Field of Classification Search

CPC ...... A61B 8/485; A61B 8/5223; G06N 3/045; G06N 3/0464; G06N 3/08; G06N 3/09

See application file for complete search history.

(56) References Cited

U.S. PATENT DOCUMENTS

| | | | | |
|---|---|---|---|---|
| 2009/0034808 | A1* | 2/2009 | Zhou | G06F 18/214<br>382/128 |
| 2020/0069292 | A1 | 3/2020 | Abolmaesumi | |
| 2020/0074625 | A1* | 3/2020 | Østvik | G06F 18/2163 |

FOREIGN PATENT DOCUMENTS

| | | | |
|---|---|---|---|
| JP | 2021506541 | A | 2/2021 |
| JP | 2021531885 | A | 11/2021 |
| JP | 2022519979 | A | 3/2022 |
| JP | 2022553614 | A | 12/2022 |
| WO | 2011083789 | A1 | 5/2013 |
| WO | 2019115652 | A1 | 6/2019 |
| WO | 2020020809 | A1 | 1/2020 |
| WO | 2020121014 | A1 | 6/2020 |

* cited by examiner

| Model | Dice Coefficient(%) |
|---|---|
| Non-contrast A2C/A4C views | 92.47 |

ASSESSING HEART PARAMETERS USING NEURAL NETWORKS

FIELD OF THE INVENTION

The present invention relates to a neural network for determining a parameter of the human heart from a plurality of echocardiogram images.

BACKGROUND

Echocardiography is a powerful tool for investigating heart conditions but it has traditionally relied heavily upon interpretation of the resulting images by expert radiographers. This results in delay and expense.

In echocardiography, ultrasound data for a particular patient's heart is usually collected for a number of different "views", that is data collected by a probe from different points around the patient's body such that each view represents a different plane through the patient's body. These views may include an apical four-chamber view, apical three-chamber view, apical two chamber view and parasternal long axis and short axis views. Sometimes all of the views will be present in patient data and sometimes only a subset is available. There may also be multiple ultrasound videos for a single view in respect of a particular patient. Ultrasound results are often communicated by way of a DICOM (Digital Images and Communication in Medicine) file although the skilled reader will appreciate that other formats are available.

Some work has already been done on interpreting individual ultrasound views using trained neural networks, for example to automatically contour the walls of the heart. However, such neural networks only operate with a particular view (such as the apical four-chamber view, for example) meaning that any particular network can only accept ultrasound data pertaining to one type of input data (i.e. one "view").

Unfortunately, ultrasound files such as DICOM files do not typically include any information regarding which view is present in any particular set of data. It can take a human operator up to 20 minutes or more to classify all of the ultrasound data from a particular patient to ensure that data relating to the correct view is provided to the correct neural network and derive clinically applicable cardiac measurements.

It is an object of the present invention to ameliorate this drawback.

SUMMARY OF THE INVENTION

According to a first aspect of the present invention there is provided a system for providing a parameter of a human heart, the system comprising: a first trained neural network having an input and an output, the first neural network arranged to receive a plurality of echocardiographic images and to classify the echocardiographic images into one of at least two different views comprising at least a two-chamber view and a four-chamber view, and a second trained neural network having an input and an output, the second neural network arranged to receive images from at least one of the two-chamber or the four-chamber view and to identify the endocardial border of the left ventricle for each view, a first responder, which is responsive to the outputs of the second neural network to identify end-systole and end-diastole images, and a second responder, which is responsive to the end-systole and end-diastole images to derive a parameter of the heart.

By automatically detecting the relevant view in the source data and segmenting the left ventricle endocardial border a more accurate and efficient system is provided. By automatically providing a parameter, a physician or subsequent automated system can more easily and efficiently diagnose the patient.

Most parameters require the endocardial border of the left ventricle to be outlined (segmentation), with the combination of at least the two and four-chamber views to form a volume, such as the Simpson's biplane method to determine ventricular volume additionally required to calculate parameters such as ejection fraction.

From the left ventricle segmentation, suitable parameters which include ejection fraction (EF) and global longitudinal strain (GLS) are derived. Additionally or alternatively, local (regional) strain values may be derived. The view detection network may provide a confidence measurement together with the decision as to which view is present. This measure may be used to eliminate any superfluous views (i.e. 3-chamber apical and SAX views) and/or to select one set of views from multiple sets of the same type of view.

The first responder may be a means which is responsive to the outputs of the second neural network to identify end-systole and end-diastole images. The second responder may be a means responsive to the outputs of the second neural network to identify end-systole and end-diastole images.

According to a second aspect of the present invention there is provided a method of diagnosing a pathology of a heart comprising: receiving a plurality of echocardiographic images from a subject, using the system of the first aspect to analyse the plurality of echocardiographic images to derive a parameter of the heart, comparing the parameter of the heart to a at least one predetermined threshold parameter, and detecting a difference between the parameter of the heart and the at least one threshold parameter, said difference being indicative of a pathology of the heart.

According to a third aspect of the present invention there is provided a method of treating a pathology of a heart comprising: receiving a plurality of echocardiographic images from a subject, using the system of the first aspect to analyse the plurality of echocardiographic images to derive a parameter of the heart, comparing the parameter of the heart to a at least one predetermined threshold parameter, detecting a difference between the parameter of the heart and the at least one threshold parameter, said difference being indicative of a pathology of the heart, and administering a therapeutically effective amount of a drug to the subject, the drug alleviating one or more symptoms of the pathology of the heart.

The methods and systems of the present invention may be implemented on a conventional echocardiography device or may be implemented as a standalone system that receives echocardiography data.

BRIEF DESCRIPTION OF THE FIGURES

The present invention will now be described by way of example with reference to the following figures.

DETAILED DESCRIPTION

Figure 1:
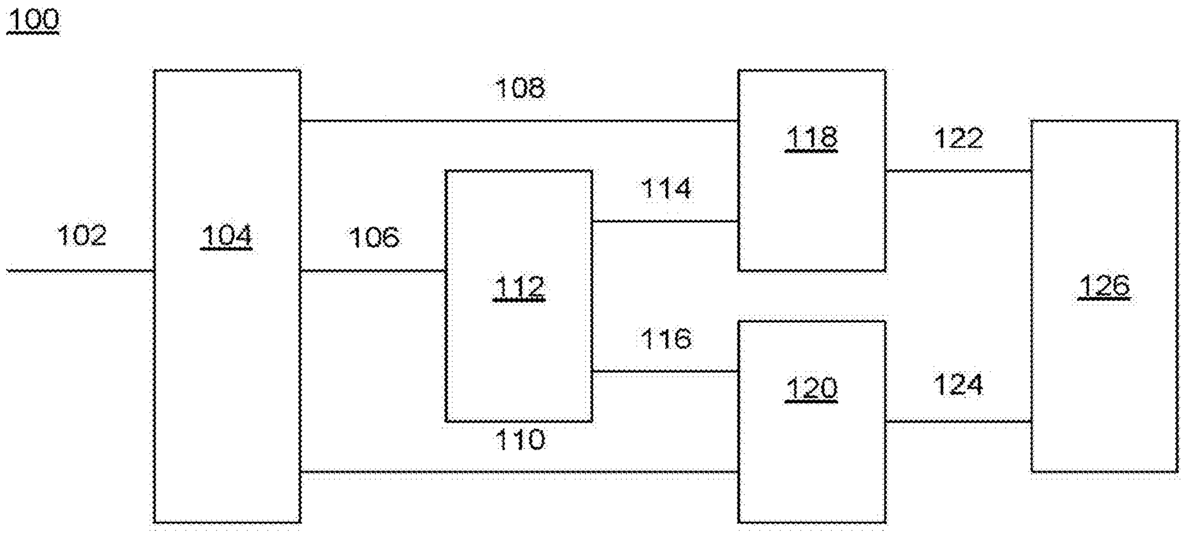
FIG. 1 is a block schematic diagram showing a first arrangement of neural networks according to an embodiment of the present invention.

FIG. 1 shows a system 100 in which input ultrasound images 102 are provided to a first trained neural network 104. Apparatus for obtaining ultrasound images is illustrated for example in WO2017/216545 and well-known commercial systems are available from companies which include Philips, Siemens and General Electric. In this example, the input to the embodiment comprises a plurality of non-contrast echocardiographic video clips consisting of multiple instances of acquisition views with a given subject's DICOM imaging study. In an alternative example, the input to the embodiment comprises a plurality of contrast echocardiographic video clips consisting of multiple instances of acquisition views with a given subject's DICOM imaging study. Of course, other imaging formats may be used as required.

There are two broad categories of imaging modality known to those skilled in the art of echocardiography. These are known as contrast and non-contrast imaging. Contrast echocardiography describes a range of imaging approaches, all of which rely on the introduction of contrast agents which are acoustically active and persist in the vascular space for a period of time. In some embodiments of the present invention, the contrast echocardiographic images are echocardiographic images which have been obtained during or after the introduction of one or more acoustically active contrast agents. Contrast images may be obtained by introducing a contrast agent such as microbubbles into the patient. Contrast agents, in general, improve the detection of the ventricular border in echocardiographic images compared to non-contrast echocardiographic images, which are echocardiographic images captured from a subject who has not been administered with a contrast agent. Non-contrast imaging involves the collection of echocardiographic images in the absence of any contrast agent.

In some embodiments, any aspect of the present invention utilizes non-contrast echocardiographic images. In some other embodiments, any aspect of the present invention utilizes contrast echocardiographic images. In some embodiments, any aspect of the present invention utilizes both contrast and non-contrast echocardiographic images. The systems and methods described herein, and their embodiments, readily apply to both imaging modalities.

The first neural network 104 is arranged to determine which view the input video clip relates to so that it can be provided to and processed correctly by the subsequent stages of the system.

Preferably the first neural network also provides a confidence measure for the determination of the relevant view, i.e. an indication of how likely the view is actually of the determined type.

In this example, only the 2-chamber apical view and the 4-chamber apical view are required. Consequently, any views that relate to other types of view such as 3-chamber apical views or SAX views are ignored. This may be done in two different ways.

The first neural network may be trained to identify any number of possible views, e.g. 2-chamber apical, 3-chamber apical, 4-chamber apical and parasternal short-axis (SAX) views. It is then straightforward to pass only the 2-chamber apical and the 4-chamber apical views to the subsequent processing stages.

Alternatively, the first neural network may be trained to identify only 2-chamber apical and 4-chamber apical views together with a confidence measure for each one. This means that, for example, 3-chamber apical and SAX views may be (wrongly) classified as 2-chamber apical or 4-chamber apical views by the neural network. However, the confidence measure associated with these erroneous classifications should be low. Data having a low confidence measure is then ignored, meaning that only the 2-chamber apical and 4-chamber apical data is passed to the subsequent processing stages.

Two or four-chamber apical data 106 is thus provided to a second convolutional neural network 112 trained to contour the left ventricle of each input view. Other methods for providing the data to the second neural network will be apparent to the skilled reader. For example, all of the image data may be provided to a second neural network, but the neural network will only be activated to process the correct image(s) in response to an output from the view detection neural network 104. The first neural network 104 also provides an indication 108 that it has detected a 2-chamber view and provides an indication 110 that it has detected a 4-chamber view.

Figure 3:
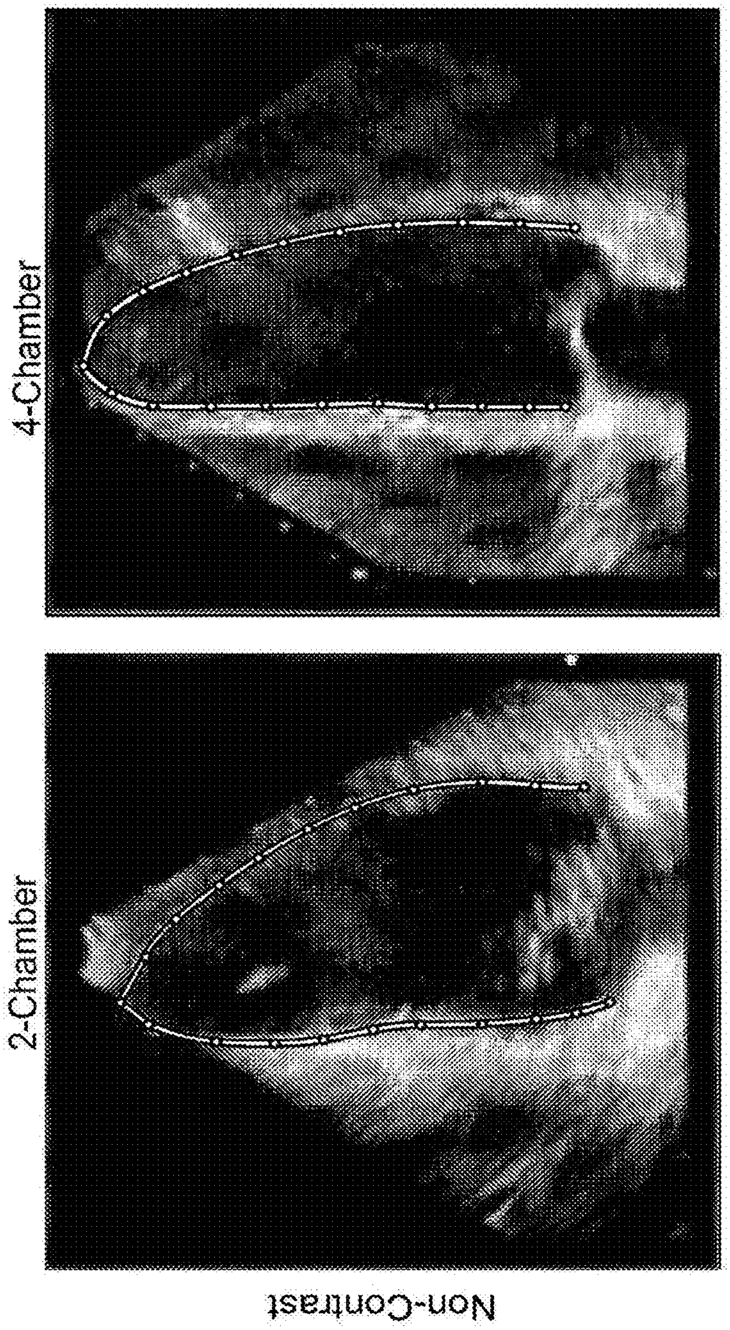
FIG. 3 shows the contouring of the left ventricle using an embodiment of the present invention.

The second network 112 determines the contour of the endocardial border for the left ventricle in the respective images. FIG. 3 shows an example of such contouring tracked around the endocardial border.

Once the endocardial border has been contoured for each of the input images, the two-chamber view 114 and four-chamber view 116 are provided to a first responder 118 and 120, which can undertake respective cycle and frame selection operations. In other words, the two-chamber view 114 and four-chamber view 116 are provided to respective cycle and frame selection means 118 and 120. The first responder is arranged to determine the end-systole and end-diastole frames in the image data. In an example, the image data comprises non-contrast image data. In an alternative example, the image data comprises contrast image data. Knowing which frames relate to the fully-contracted or fully-dilated left ventricle may then be used to determine key parameters such as the ejection fraction (EF) and the global longitudinal strain (GLS) for the subject heart. Other parameters may also or alternatively be determined such as any one or more of volume, principal strain, shear strain, regional strain, left ventricular mass, left ventricular area, left ventricular length, rectangularity, and solidity. The heart may be bovine, equine, porcine, murine, feline, canine or primatal. The skilled person appreciates that the heart may include but not be limited to a heart in a livestock animal. The skilled person further understands that the a primatal heart may include, but not be limited to, a human heart.

A first output 122 of the first responder for 2-chamber cycle and frame selection (i.e. 2-chamber cycle and frame selection means) 118 and a second output 124 of the first responder for 4-chamber cycle and frame selection (i.e. 4-chamber cycle and frame selection means) 120 are provided to a second responder 126, which can undertake parameter calculations. The second responder 126 calculates one or more parameters from any of volume, ejection fraction, global longitudinal strain, principal strain, shear strain, regional strain, left ventricular mass, left ventricular area, left ventricular length, rectangularity, and solidity. In other words, the output 122 from the 2-chamber cycle and frame selection means 118 and the output 124 of the 4-chamber cycle and frame selection means 120 are provided to a parameter calculation means 126 which calculates the parameter. For example, the ejection fraction is calculated using volume estimates, such as Simpson's biplane method. Other methods of volume calculation may also be applied.

For GLS, end-diastole (base length) and end-systole (shortened length) is used to calculate global longitudinal strain as follows:

Global longitudinal strain (%)=((shortened length-base length)/(base length))×100

In addition to GLS, regional strain parameters may be derived. Regional strain is computed by dividing the left and right sides (anterior and posterior walls) of the 2/4 chamber view contours about the apical point into three segments-making six segments for the contour in total. The regional strain at each time point for each segment is computed by taking the length of each contour segment, subtracting the length that contour segment at end-diastole, taking the ratio between this difference and the end-diastolic length, and multiplying by 100 to produce a percentage strain. This is expressed formally as:

$$s_{i,t} = \frac{l_{i,t} - l_{i,t_0}}{l_{i,t_0}} \times 100$$

Where t is the time index relative to the end-diastolic time frame at $t_0$ and $l_i$ are the lengths of the $i^{th}$ contour segments.

The regional strains through time generally produce a curve that starts and ends at around a value of zero for the end-diastolic time-points. These are then temporally smoothed to account for errors. The output parameters are then the strain curves for each segment, the peak strain (i.e. the most negative strain value in each curve) for each segment and the time between the starting end-diastolic time-point and the peak strain-referred to as "time to peak". The end systolic strain values may also be calculated from the identified end systolic and end diastolic frames.

The first responder 118, 120 may be a cycle and frame selection means. It may also make use of other data such as ECG traces to identify the end-systole and end-diastole frames in the contoured image data.

The two neural networks shown in FIG. 1 are trained separately as follows. The first (view detection) neural network is provided with training ultrasound data in which the relevant view has been identified by human operators. In an example, the training ultrasound data comprises non-contrast ultrasound data. In an alternative example, the training ultrasound data comprises contrast ultrasound data.

From a sufficiently large multiple subject DICOM dataset several apical-4-chamber (A4C), apical-3-chamber views (A3C), apical-2-chamber (A2C) and parasternal short-axis mitral-valve (PSAX-MV or SAX) views were present within each subject's DICOM study. The first neural network comprises a multi-class convolutional neural network (CNN) arranged to receive as an input a plurality of echocardiographic video clips. In an example, the echocardiographic video clips comprise non-contrast echocardiographic video clips. In an alternative example, echocardiographic video clips comprise contrast echocardiographic video clips. The first neural network is further arranged to determine whether an image was apical-4-chamber (A4C), apical-3-chamber (A3C), apical-2-chamber (A2C) and parasternal short-axis mitral-valve (PSAX-MV) view. In an example, this comprised using multiple 2D convolutional layers using grayscale image inputs. Cross-entropy was used as the loss function. Class-weighting factors were applied to data to match the uneven distribution of the training data for each view represented. Inference using the classifier model was performed on all frames within an image study to assess which view the study was, with the sum of the classifier output used as a class voting strategy. For preliminary validation in an example where the echocardiographic video clips were comprised of non-contrast echocardiographic video clips, an unseen "holdout" data subset formed of 10% of the original data was applied to the view classifier to produce a view identification accuracy shown in Table 1 below. The true label is located on the vertical axis and the predicted label (by the neural network) is located on the horizontal axis. There was only some slight misclassification between the 2C and 3C views.

TABLE 1

| | 2C | 3C | 4C | SAX |
|---|---|---|---|---|
| 2C | 0.99 | 0.01 | 0.00 | 0.00 |
| 3C | 0.01 | 0.99 | 0.00 | 0.00 |
| 4C | 0.00 | 0.00 | 1.00 | 0.00 |
| SAX | 0.00 | 0.00 | 0.00 | 1.00 |

For preliminary validation in an example where the echocardiographic video clips were comprised of contrast echocardiographic video clips, an unseen "holdout" data subset formed of 10% of the original data was applied to the view classifier to produce a view identification accuracy shown in Table 2 below. As in Table 1, the true label is located on the vertical axis and the predicted label (by the neural network) is located on the horizontal axis. There was only some slight misclassification between the 2C and 3C views.

TABLE 2

| | 2C | 3C | 4C | SAX |
|---|---|---|---|---|
| 2C | 0.90 | 0.01 | 0.08 | 0.00 |
| 3C | 0.05 | 0.95 | 0.00 | 0.00 |
| 4C | 0.05 | 0.00 | 0.94 | 0.00 |
| SAX | 0.00 | 0.00 | 0.00 | 1.00 |

In an example where the echocardiographic video clips were comprised of non-contrast echocardiographic video clips, the view classifier was also tested using an independent test dataset and the results were as shown in Table 3.

TABLE 3

| | 2C | 3C | 4C | SAX |
|---|---|---|---|---|
| 2C | 0.97 | 0.02 | 0.01 | 0.00 |
| 3C | 0.01 | 0.99 | 0.00 | 0.00 |
| 4C | 0.01 | 0.00 | 0.99 | 0.00 |
| SAX | 0.01 | 0.00 | 0.00 | 0.99 |

In an example where the echocardiographic video clips were comprised of contrast echocardiographic video clips, the view classifier was also tested using an independent test dataset and the results were as shown in Table 4.

TABLE 4

| | 2C | 3C | 4C | SAX |
|---|---|---|---|---|
| 2C | 0.85 | 0.01 | 0.12 | 0.01 |
| 3C | 0.04 | 0.96 | 0.00 | 0.00 |
| 4C | 0.07 | 0.00 | 0.93 | 0.00 |
| SAX | 0.00 | 0.01 | 0.01 | 0.99 |

The left ventricle (LV) segmentation algorithm comprised a U-net convolutional neural network (CNN) auto-LV segmentation framework developed using Python 3.5 with Keras (Chollet, Francois et. Al. 2015, htts://keras.io) and Google Tensorflow: A system for large-scale machine learning (Abadi, Martin et al., 2016 12th USENIX Symposium on Operating Systems Design and Implementation n (OSDI 16), page 265-283, https://www.usenix.org/system/files/conference/osdi16/osdi16-abadi.pdf) backend to segment A2C and A4C views. In an example, non-contrast A2C and A4C views were segmented. In an alternative example, contrast A2C and A4C views were segmented. Images were used to train the U-net CNN initially contoured (i.e. LV endocardial border traced) manually by British Society of Echocardiography (BSE) accredited echocardiographers. In an example, non-contrast images were used to train the U-net CNN. In an alternative example, contrast images were used to train the U-net CNN. The images comprised frames for A2C and A4C views, respectively. Both datasets were split into 80% training and 20% validation sets for training the CNN. Raw images were filtered, normalised and applied to the modified U-net CNN framework. The CNNs produce contours that were able to track the endocardial walls smoothly through time (FIG. 3). The efficacy of the network's segmentation performance was assessed using the Sørensen-Dice Coefficient (DC) which is computed from the ratio of the intersection of the output contours (Y) and the known ground truth contours (X) as shown below:

$$DC = 2|X \cap Y|/(|X| + |Y|)$$

The LV contours (segmentations) represent the output of this algorithm and input for the Cycle and Frame Selection stages.

A plurality of LV contours are received into the Cycle and Frame Selection algorithm, derived from the preceding LV segmentation algorithm. To automatically calculate parameters such as EF and GLS it is necessary to automatically identify the cardiac cycle and end-diastole and end-systole frames, before computing physiological measures. An automated method was established from the image clips comprising assessment of the heart rate (generally available in the DICOM file as a DICOM tag), the number of frames (also generally available in the DICOM file as a DICOM tag), a series of contours, one per frame, for the view under consideration. The method is summarised in FIG. 4, and consists of separation of cycles, filtering of cycles and extraction of end-diastole (ED) and end-systole (ES) frames, and filtering of systole cycles. The resulting series of contours may be from a single cardiac cycle, or from multiple cardiac cycles. The first step is to separate the series of contours into multiple cardiac cycles, when possible. It is possible to calculate the number of complete cardiac cycles using a simple formula:

$$\text{numcycles}=(\text{timebetweenframes})\times(\text{heartrate})\times(\text{numframes})$$

Where "timebetweenframes" is the time between individual frames. Once the ES and ED frames are identified, image features are extracted from the two contours generated for each view as the output of this algorithm for input into the Anatomical Quantification algorithm.

In an example, all of the training data was based on non-contrast echocardiograms. In an alternative example, all of the training data was based on contrast echocardiograms.

Figure 2:
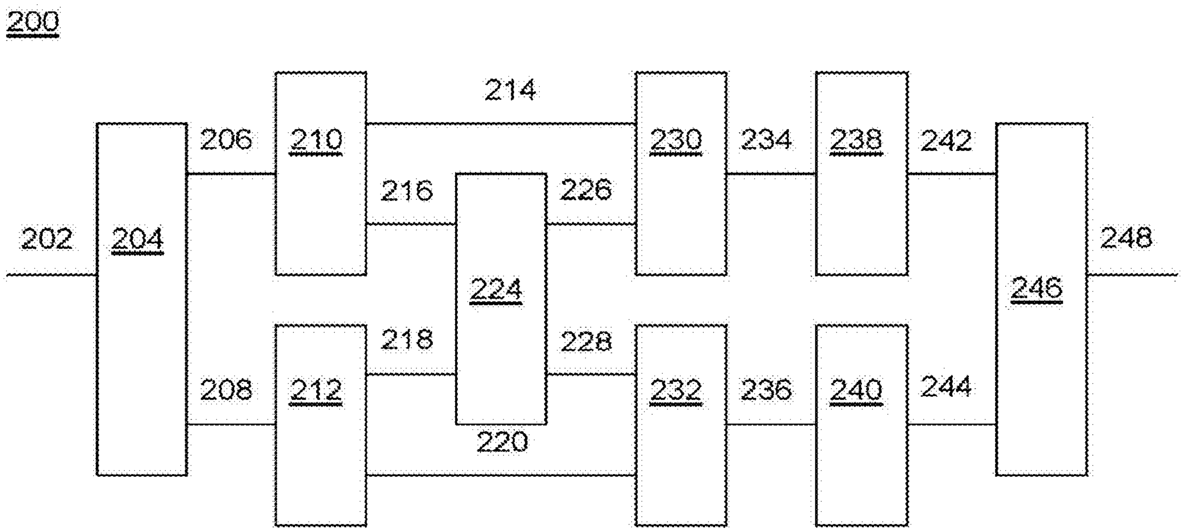
FIG. 2 is a block schematic diagram of a second embodiment of the present invention that comprises six processing stages connected in series.

FIG. 2 shows a second embodiment of the present invention which differs from the first embodiment mainly by inclusion of a clip selection algorithm in each path. FIG. 2 shows the embodiment 200 in which six processing stages are applied to the input views. A plurality of image files 202 is provided to a first neural network 204 trained to perform view detection as previously discussed with reference to FIG. 1. In an example, the image files are comprised of non-contrast images. In a second example, the image files are comprised of contrast images. The first neural network 204 may also provide a confidence measure which indicates the degree of confidence that the category into which a video clip has been placed is correct. In this embodiment the first neural network has been trained using 2-chamber apical, 3-chamber apical, 4-chamber apical and SAX views.

The output of the first network comprises identified two-chamber views 206 and identified four-chamber views 208 which are provided to respective Video Clip Selection algorithms 210, 212. In an example, the video clip selection algorithms are arranged to select the best of (possible) multiple ultrasound videos for each view to provide to the subsequent processing stages. In This may be done on the basis of the confidence measure. In an alternative example, the video clip selection algorithms are arranged to select suitable videos of multiple ultrasound videos of multiple ultrasound videos for each view to provide to the subsequent processing steps. This may be done on the basis of at least one characteristic of the echocardiographic images. The at least one characteristic comprises at least one of the confidence measure, gain, granularity, resolution, level of motion in the image, the field-of-view, the size of the field-of-view, the size of the image, or the number of chambers in a given view. The outputs 214, 216 of the Video Clip Selection algorithm 210 are connected respectively to the inputs to a frame selection stage 230 and a Left Ventricle (LV) Segmentation neural network 224. The outputs 218, 220 of the Video Clip Selection algorithm 212 are connected respectively to the inputs to the Left Ventricle (LV) Segmentation neural network 224 and a frame selection stage 232. The output 226, 228 of this neural network is provided as input to respective Cycle and Frame selection algorithms 230, 232. These algorithms provide their outputs 234, 236 as input to respective Anatomical Quantification algorithms 238, 240 which provide outputs 242, 244 to a combination algorithm 246. The combination algorithm provides an output parameter 248. The output parameter may be one or more of ventricle volume, ejection fraction, global longitudinal strain, principal strain, shear strain, regional (local) strain, left ventricular mass, left ventricular area, left ventricular length, rectangularity, and solidity.

The separation of the neural networks means that the network designer can be confident that subsequent model training and application has accounted for the variables associated with different echocardiographic views, in this example, or any other preceding confounders that have been addressed in a previous step.

Figure 4:
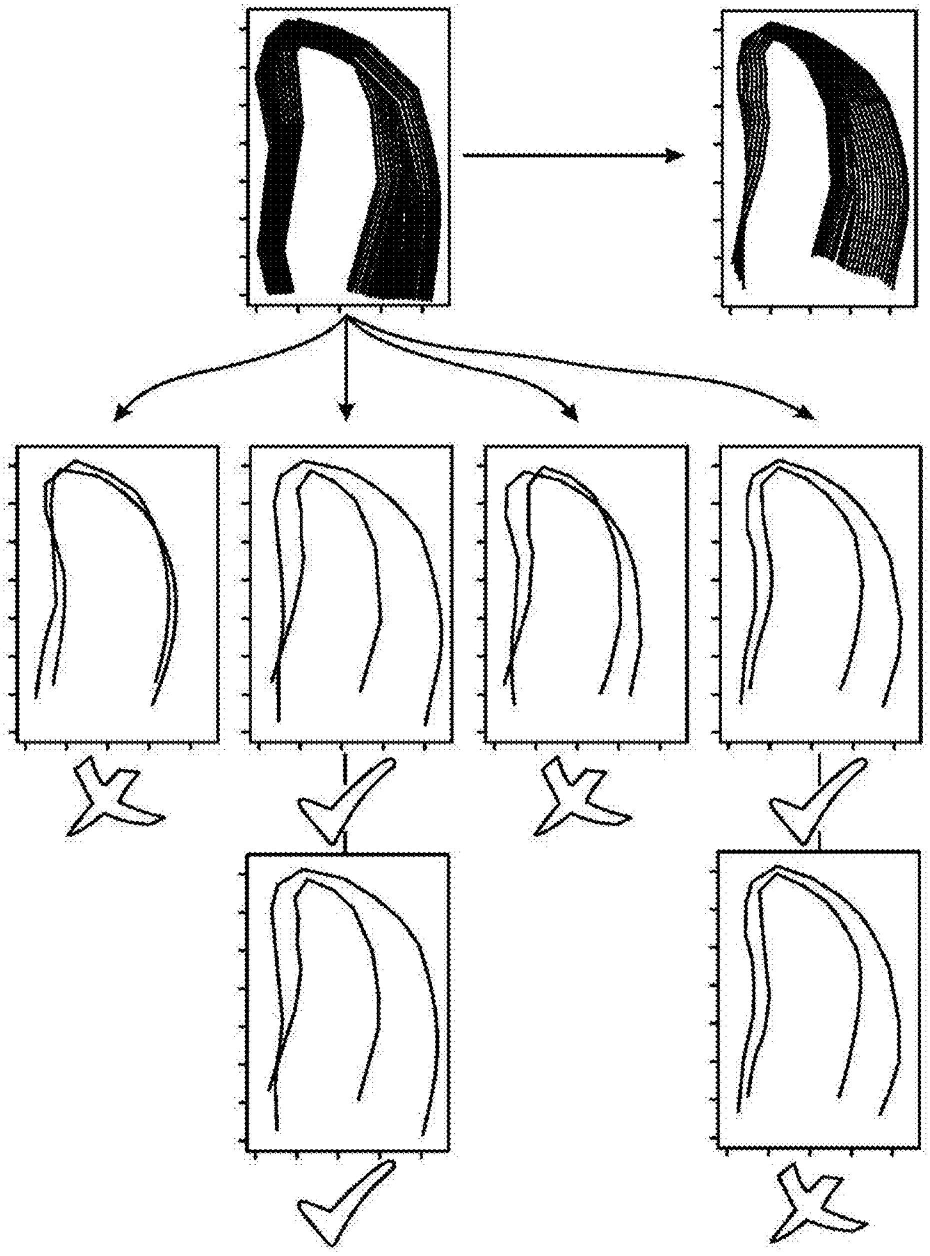
FIG. 4 illustrates the selection process of end-diastole and end-systole frames identified by an embodiment of the present invention.
Figure 5:
FIG. 5 shows end-diastole and end-systole frames identified by an embodiment of the present invention.

FIG. 4 shows the process for identifying ED and ES frames as follows. The end-diastole and end-systole contours are extracted from a set of contours by considering many possible end-diastole and end-systole candidates (top row diagrams). After this filtering, the candidate with the largest area difference is chosen (bottom row of diagrams). See also FIG. 5.

The process is repeated for both the 2-chamber apical view and the 4-chamber apical view.

Taking the ED and ES selected frames from the Cycle and Frame selection algorithms as an input, a physiological parameter such as volume, ejection fraction or global longitudinal strain may be calculated as described. Additionally, or alternatively, any one or more of principal strain, shear strain, regional strain, left ventricular mass, left ventricular area, left ventricular length, rectangularity, and solidity may be calculated.

Ejection fraction and global longitudinal strain are well known parameters in echocardiography useful for detecting abnormalities in the heart of a subject e.g. heart failure, coronary artery disease, amyloidosis, and hypertrophic cardiomyopathy. The system described above can be used in a method of determining an indication of the prognosis of a subject with a cardiac abnormality. Additionally or alternatively, the system described above can be used in a method of diagnosing a pathology of a heart. Additionally, the system as described above can be used in a method of treating a pathology of a heart. A series of echocardiographic images from a subject would be analysed by the above-described system in order to derive a parameter. In an example, the series of echocardiographic images comprise a series of non-contrast echocardiographic images. In an alternative example, the series of echocardiographic images comprise a series of contrast images. The parameter of the heart that is derived could be one or more of volume, ejection fraction, global longitudinal strain, principal strain, shear strain, regional strain, left ventricular mass, left ventricular area, left ventricular length, rectangularity, and solidity, which are known in the art. In an example, once the one or more parameters are derived by the system, they would be compared to a reference data set. This reference data set could comprise a plurality of reference contrast echocardiographic images which have been analysed by the system previously in order to produce a threshold parameter. In an alternative example, once the one or more parameters are derived by the system, they would be compared to at least one predetermined threshold parameter. Optionally, the predetermined threshold parameter is derived from a plurality of reference non-contrast echocardiographic images which have been analysed by the system previously in order to produce the threshold parameter. Optionally, in an alternative example, the predetermined threshold parameter is derived from a plurality of reference contrast echocardiographic images which have been analysed by the system previously in order to produce the threshold parameter. Additionally or alternatively, in an example, the at least one predetermined threshold parameter is derived from known medically defined parameters. In any of the examples described previously, the predetermined threshold parameter could be one or more of volume, ejection fraction, global longitudinal strain, principal strain, shear strain, regional strain, left ventricular mass, left ventricular area, left ventricular length, rectangularity, and solidity.

The plurality of reference echocardiographic images could be from subjects who do not have a pathology of the heart. In this instance, the threshold parameter would represent a normal value, and deviation from this value would be indicative of a pathology of the heart.

The plurality of reference echocardiographic images could be from subjects who have a known pathology of the heart. In this instance, the threshold parameter would represent an abnormal value, and if the parameter of the subject for which the system is being used is within a set range of the threshold, this would be indicative of the known pathology of the heart.

The plurality of reference echocardiographic images could be from subjects with a known pathology, and subjects without a known pathology. As the predetermined threshold parameter may be derived from a plurality of reference echocardiographic image, predetermined threshold parameter could be updated over time to reflect newly diagnosed pathologies in the subjects.

The comparison between the parameter derived for the subject, and the threshold derived from the reference data set or from the predetermined threshold parameter could be performed by a physician, who would then decide whether or not a pathology of the heart is present in the subject and/or the prognosis of the subject based on the comparison. Alternatively, the comparison could itself be performed by a system suitable for that purpose. Such systems are disclosed in WO 2017/216545 A1. The diagnosis of a pathology of the heart, such as heart failure, could be made by the physician, by the system, or by the two working in tandem.

Once a diagnosis of a pathology of a heart (e.g. heart failure) has been obtained then a prescription for remediation may be derived such as a prescription for pharmaceuticals and/or lifestyle changes.

The present invention also includes a method of treating a pathology of a heart in a subject, comprising obtaining a diagnosis of a pathology of the heart in a subject as described above, and then administering, to the subject, a therapeutically effective amount of a drug to alleviate the symptoms of the pathology of the heart. For example, having obtained a diagnosis of heart failure as described above, the physician would then administer a suitable treatment for heart failure. This treatment could involve the administration of one or more of angiotensin-converting enzyme (ACE) inhibitors, angiotensin receptor blockers, beta blockers, mineralocorticoid receptor antagonists, diuretics, and other commonly used drugs for the treatment of heart failure. The exact selection and dosage for the treatment depend on the clinical history of the subject, but would be readily apparent to a person skilled in the art.

As an example, using a system as described above, a physician derives the ejection fraction (EF) of the left ventricle of the heart of a patient, and compares it to a reference data set derived from a plurality of reference echocardiographic images of subjects without a pathology of the heart. The ejection fraction is significantly reduced compared to the reference data set, indicating heart failure. The physician therefore administers a course of ramipril (an ACE inhibitor), with an initial dosage of 1.25 mg daily, which is slowly increased under supervision to 10 mg daily.

As alternative example, using a system as described above, a physician derives the ejection fraction (EF) of the left ventricle of the heart of a patient, and compares it to a predetermined threshold parameter. Optionally, the predetermined threshold parameter is derived from a plurality of reference non-contrast echocardiographic images of a subject without pathology of the heart. Optionally, in an alternative example, the predetermined threshold parameter is derived from a plurality of reference contrast echocardiographic images of a subject without pathology of the heart.

Additionally or alternatively, in an example, the at least one predetermined threshold parameter is derived from known medically defined parameters. The ejection fraction is significantly reduced compared to the corresponding threshold parameter, indicating heart failure. The physician therefore administers a course of ramipril (an ACE inhibitor), with an initial dosage of 1.25 mg daily, which is slowly increased under supervision to 10 mg daily.

Applying a sequential series of AI algorithms to an image processing problem overcomes the problem of poor reproducibility in image quantification that exists in traditional echocardiography quantification applications. This results in improved efficiency (fewer processing failures) and improved outcomes (patient benefit in this case).

Figure 6:
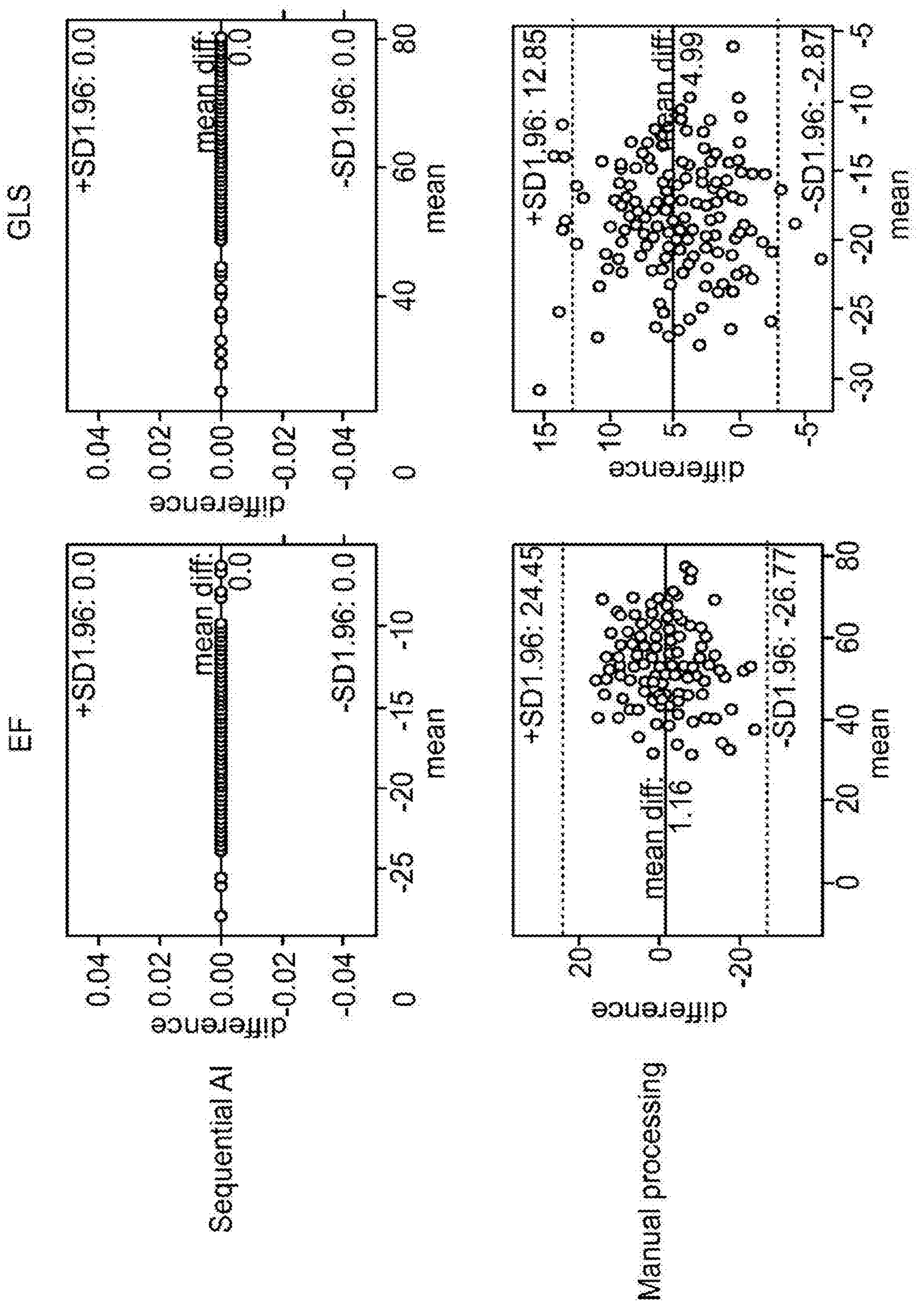
FIG. 6 shows a comparison between an embodiment of the present invention and traditional human processing of cardiac image data.

To illustrate this, the accuracy and precision of the described embodiment was assessed against traditional human operators performing routine image processing methodology (i.e. manual view, cycle and frame selection with manual LV segmentation and physiological parameter computation). Data was collected consisting of a series of Digital Imaging and Communications in Medicine (DICOM) format videos visualizing the heart from different angles (views). From the collated dataset the above described approach was applied to quantify exemplar physiological measures (ejection fraction (EF) and global longitudinal strain (GLS)) using apical-4-chamber (A4C) and apical-2-chamber (A2C) videos. In addition, the same above data were processed for left ventricle (LV) quantification by qualified echocardiographers (operators). Using data processed multiple times by several different operators, we compare the repeatability (defined as the difference in measurement provided by operators processing the same image studies through repeatedly). From this study, we demonstrate that autonomous sequential AI image processing dramatically reduces the variability in two key assessors of LV function: EF, and GLS (FIG. 6). This is achieved by relying on full automation when outlining the endocardial border.

The term "neural network" is used herein to denote a network that is trained on a set of data. If a portion of a particular network is trained independently from the remainder of the network then that portion of the network is regarded as a "neural network" and the overall particular network would comprise two (or more) "neural networks".

The invention claimed is:

1. A system for providing a parameter of a human heart, the system comprising:
- a first trained neural network arranged to:
  - receive a plurality of echocardiographic images; and
  - identify at least one of a two-chamber view or a four-chamber view in the plurality of echocardiographic images;
- a third responder arranged to:
  - select, based on at least one characteristic of the echocardiographic images, a subset of images for a given view, wherein the at least one characteristic is at least one of gain, granularity, resolution, level of motion in the image, the field-of-view, the size of the field-of view, the size of the image, or the number of chambers in the given view;
  - generate a first output based on the subset of images;
- a second trained neural network arranged to:
  - receive the first output;
  - contour the first output by identifying the endocardial border of the left ventricle for the given view; and
  - generate a second output based on the contoured first output;
- a first responder arranged to:
  - receive the second output;
  - identify end-systole and end-diastole images based on the second output; and
  - generate a third output based on the end-systole and end-diastole images;
- a second responder arranged to:
  - receive the third output; and
  - derive at least one first parameter of the heart based on the third output, wherein the at least one first parameter is Global Longitudinal Stain, principal strain, shear strain or regional strain.

2. The system as claimed in claim 1, wherein the second responder is arranged to combine the two-chamber and four-chamber endocardial borders of the left ventricle to derive volume-based parameters.

3. The system as claimed in claim 1, wherein the regional strain parameter comprises six regions.

4. The system as claimed in claim 1, wherein the plurality of echocardiographic images comprise a plurality of non-contrast images.

5. The system as claimed in claim 1, wherein the plurality of echocardiographic images comprise a plurality of contrast echocardiographic images.

6. A method of training a system as claimed in claim 1, wherein the neural networks are trained on non-contrast data.

7. A method of training a system as claimed in claim 1, wherein the neural networks are trained on contrast data.

8. A method of diagnosing a pathology of a heart comprising:
- receiving a plurality of echocardiographic images from a subject;
- using the system according to claim 1 to analyse the plurality of echocardiographic images to derive a parameter of the heart;
- comparing the parameter of the heart to at least one predetermined threshold parameter; and
- detecting a difference between the parameter of the heart and the at least one predetermined threshold parameter, said difference being indicative of a pathology of the heart.

9. A method of treating a pathology of a heart comprising:
- receiving a plurality of echocardiographic images from a subject, using the system according to claim 1 to analyse the plurality of echocardiographic images to derive a parameter of the heart;
- comparing the parameter to at least one threshold parameter;
- detecting a difference between the parameter of the heart and the at least one predetermined threshold parameter, said difference being indicative of a pathology of the heart, and
- administering a therapeutically effective amount of a drug to the subject, the drug alleviating one or more symptoms of the pathology of the heart.

10. The system as claimed in claim 1, wherein the second responder is further configured to:
- derive one first parameter of the heart based on the end-systole and end-diastole images, wherein the one first parameter is Global Longitudinal Strain, principal strain, shear strain, or regional strain; and
- derive a second parameter of the heart based on the end-systole and end-diastole images, wherein the second parameter of the heart is the ejection fraction.

11. The system as claimed in claim 1, wherein the first responder is further configured to:

identify one or more cardiac cycles, wherein the third output is further based on the identified one or more cardiac cycles.

* * * * *